United States Patent [19]
Waldhauer

[11] Patent Number: 5,357,171
[45] Date of Patent: Oct. 18, 1994

[54] GAS DISCHARGE LAMP SYSTEM WITH AUTOMATIC SHUTOFF MEANS

[75] Inventor: Lothar Waldhauer, Lohhof, Fed. Rep. of Germany

[73] Assignee: Heraeus Noblelight GmbH, Hanau, Fed. Rep. of Germany

[21] Appl. No.: 959,670

[22] Filed: Oct. 13, 1992

[30] Foreign Application Priority Data

Oct. 10, 1991 [DE] Fed. Rep. of Germany ........ 4133614

[51] Int. Cl.$^5$ ............................................. H05B 37/02
[52] U.S. Cl. .................................... 315/151; 315/158; 315/159; 313/27
[58] Field of Search ........................ 315/158, 151, 159; 313/27, 571, 638, 639, 25, 229; 250/205

[56] References Cited

U.S. PATENT DOCUMENTS

| | | | |
|---|---|---|---|
| 3,234,421 | 2/1966 | Retling | 313/27 |
| 4,074,164 | 2/1978 | Leyendecker | 313/25 |
| 4,155,025 | 5/1979 | Dobrusskin et al. | 313/229 |
| 4,431,947 | 2/1984 | Ferriss et al. | 315/151 |
| 4,463,284 | 7/1984 | Tamura et al. | 315/158 |

FOREIGN PATENT DOCUMENTS

| | | |
|---|---|---|
| 2616893 | 11/1977 | Fed. Rep. of Germany . |
| 3121689A1 | 12/1982 | Fed. Rep. of Germany . |
| 3121689C2 | 7/1983 | Fed. Rep. of Germany . |
| 3729711A1 | 3/1989 | Fed. Rep. of Germany . |

OTHER PUBLICATIONS

CRC Handbook of Chemistry and Physics, 52nd Edition (p. E-193).

Primary Examiner—Robert J. Pascal
Assistant Examiner—Haissa Philogene
Attorney, Agent, or Firm—Frishauf, Holtz, Goodman & Woodward

[57] ABSTRACT

A gas discharge lamp has a fill mixture with first radiation-emitting substances which emit predominantly in an ultraviolet spectral range, and a further radiation-emitting substance which has an emission line in a lower-frequency spectral range. The intensity at the lower-frequency emission line is monitored and used to control lamp operation. This prevents continued use of lamps whose normal service life has been exceeded, as evidenced by intensity dropoff or frequency drift. This in turn prevents damage to health, in lamps used for medical or cosmetic purposes, or malfunctions in technical manufacturing processes, in lamps used in such processes. Thus, irradiation with unsuitable discharge tubes is prevented. Depending upon the intended lamp application, preferred fill additives may include lithium, cesium, thallium, or sodium.

9 Claims, 2 Drawing Sheets

GAS DISCHARGE LAMP SYSTEM WITH AUTOMATIC SHUTOFF MEANS

Cross-reference to related patent, the disclosure of which is hereby incorporated by reference: U.S. Pat. No. 4,155,025, 15 May 1979.

FIELD OF THE INVENTION

The present invention relates generally to a gas discharge lamp, and, more particularly, to an ultraviolet-emitting lamp having a fill which generates a non-ultraviolet emission line which serves as a "marker" of performance of the lamp as made.

BACKGROUND

Gas discharge lamps contain a gas mixture fill or filling which is excited, by the electrical discharge through the gas, into emission of radiation. Fluorescent lamps additionally have a phosphor coating on the inside of the discharge tube, which coating converts the short-wavelength (typically ultraviolet) radiation produced by the gas discharge into longer wavelength radiation (typically visible light).

For example, lamps whose radiation is intended to cause increased pigmentation of the skin (tanning) or therapeutic effects on localized diseased patches of skin, typically have gas discharge tubes whose emitted spectrum has intensity maxima in the ultraviolet region. Irradiation by the short wavelength ultraviolet B ("UVB"), which is damaging to human skin, must be avoided. This can be achieved by optimization of the gas mixture or fill placed in the discharge tube, and/or by filtering out the UVB component of the emitted radiation. UV-emitting discharge lamps operate by the familiar high pressure mercury vapor discharge, with the addition in the tube interior of metal halide compounds, in order to increase the integrated intensities of emissions in the UV-A wavelength range (315 nanometers to 380 nanometers) relative to the emissions in the UV-B wavelength range (280 nm to 315 nm). This is known from DE-OS 27 18 735 and U.S. Pat. No. 4,155,025.

In the case of lamps with discharge tubes which are used for cosmetic, medical, and technical applications, such as ultraviolet curing of plastics or graphic reproduction technology, and which therefore should have their highest emission intensity in a predetermined spectral range which is a function of the respective application, it is desirable to keep emissions in other spectral ranges as low as possible, since the non-useful emissions represent energy losses and may produce unwanted side-effects. However, not all discharge tubes available in the market satisfy these criteria.

Damage to a patient's health or malfunctions during technical manufacturing processes can be the result.

Further problems can arise, if discharge tubes continue to be used, after expiration of the normal service life specified by the manufacturer. The spectral intensity of the discharge tube may drop off substantially, or shift into other spectral ranges. Generally, the result of such use is unsatisfactory performance, or failure to achieve the expected successful result.

THE INVENTION

Accordingly, it is a primary object of the present invention to provide an improved discharge lamp in which a controlled additive permits avoiding the aforementioned disadvantages.

Briefly, a "marker" substance is added to the lamp fill. During lamp discharge, the marker generates at least one emission line, preferably at a longer wavelength/less energetic frequency than the emissions of the other substances in the fill. Clearly, one must take care that this emission line has no effect which is detrimental to the intended use application.

This marker or further radiation-emitting substances is chosen according to two primary criteria: first, it should generate one or more emission lines in a spectral range in which the other fill substances emit only weakly or have a low intensity, and, second, this emission line or lines must not have a significant detrimental effect on the quality of the irradiation which the discharge tube is primarily intended to produce. For example, if the discharge tube is intended for use in a photocopy machine, the "marker" emission line should not impair the quality of the resulting photocopies.

The further radiation-emitting substance of the invention can be added to the fill or gas mixture in the interior of the discharge tube or, alternately, if the inside of the discharge tube is coated with a fluorescing phosphor, the further substance or marker can form a component of the phosphor.

Discharge lamps according to the invention have, in their spectrum, a marking in the form of the emission line(s) of the further radiation-emitting substance.

This marking makes it possible to externally distinguish specific discharge lamps, which for example satisfy elevated quality specifications, from other lamps. Such quality specifications are placed on lamps to be used in, for example, reproduction systems or in medical ultraviolet (UV-) or infra-red (IR-) treatment. The marking permits external identification of such high-quality lamps from those which would fit in treatment systems but are qualitatively of lesser value. That is, in the quality-control stage of a production line, one can identify the high-quality lamps to be used for medical purposes, and distinguish them from the lower-quality or "reject" lamps, which can be used in less critical applications. Thus, one can avoid malfunctions in technical manufacturing processes and avoid damage to health in medical or cosmetic applications.

The invention also facilitates distinctions, among discharge tubes, according to estimated service lifetime. In the course of operation, there is a dropoff in intensity, not only of the spectra produced by the other fill substances, but also of the emission line(s) of the marker substance. The intensity of this line or lines correlates with the remaining service or operating lifetime of the discharge tube. After appropriate calibration, a measurement of the intensity of this emission line or lines permits estimation of the service life of the particular discharge tube.

A further embodiment of the invention is to place, in the discharge tube, a marker or further radiation-emitting substance whose at least one emission line is in the visible spectral range or in the infra-red spectral range, while the other fill substances emit overwhelmingly in the ultraviolet spectral range.

Here, one contemplates use of such discharge tubes in the medical or cosmetic fields. The discharge tubes used there can have an emission line in the visible or infra-red spectral range without thereby limiting their usability at all. For example, such an emission line in the visible range would merely modify the color of the radiation field of the discharge tube. Sometimes one wants to know the irradiation zone boundaries, and visible emissions help one to visualize this.

For example, using the invention, one can distinguish discharge lamps whose fill gas composition has been optimized for elevated UV-A emission and for a sharply reduced irradiation intensity in the remaining spectral range, especially the UV-B range, from those discharge lamps of lesser quality which can fit in the identical irradiation fixtures but which produce possibly health-threatening radiation.

At the same time, as previously mentioned, one can monitor the operating life of the UV discharge tubes, so that exceeding their service life can be prevented, or at least hindered.

It is advantageous if, in addition to the substances which emit predominantly in the ultraviolet range, the further radiation-emitting substance is one or more alkali metal(s) and/or one or more halide(s) of alkali metals, contained in the discharge tube.

Due to suboptimal vaporization characteristics of pure metals, one generally adds metals to discharge tubes in the form of metal halides. Discharge tubes according to the invention, which emit the major portion of their irradiation intensity in the UV-range, preferably contain one or more alkali metals, especially lithium, cesium, or sodium, or their halides. The aforementioned metals have emission lines in the visible and infra-red spectral ranges, and are thus adapted for use as the further radiation-emitting substances in a UV discharge tube according the invention.

However, the present invention is not so limited, and other metals or other chemical compounds could be found for use as the further radiation-emitting substance. Another element suitable for use in UV discharge tubes according to the invention is thallium, which has a strong emission line at 535 nm (5350 Angstroms) in the green portion of the visible spectrum.

An apparatus, for use of the discharge tube of the invention in a lamp, preferably provides an optical detector in the irradiation zone or field of the discharge tube. The output signal of the detector correlates with the intensity of one or more emission line(s) of the further radiation-emitting substance contained in the discharge tube.

The output signal of the optical detector can be transmitted to, for example, a numerical display which, during operation of the lamp, displays the existence and the amplitude of the intensity of the emission line(s) of the further radiation-emitting substance. If an irradiation system according to the invention is loaded with a discharge tube not in accordance with the invention, or with a tube whose service life has been exceeded, the output signal of the detector gives a corresponding indication. This output signal can also be converted into an optical or acoustic signal or warning, Preferably, the output signal of the optical detector stands is operatively coupled to a control means for the lamp.

Thereby, it is possible to control the operation of the lamp by means of the output signal of the detector. For example, if the level or amplitude of this output signal increases with growing intensity of the emission line(s), one can control operation of the lamp by providing that, whenever the level drops below a minimum height or threshold, which correlates with the service life of the discharge tube, or whenever no amplitude of the signal is present at all, the lamp will be shut off, since a sufficiently high irradiation quality and reliability cannot be guaranteed.

Thus, upon undershooting of the predetermined level of the output signal of the optical detector, the lamp and discharge tube are taken out of service.

An example of the invention will now be described.

DRAWINGS

FIG. 1 illustrates the spectral distribution of a so-called "iron irradiator", as used for UV irradiation. The horizontal axis shows the wavelengths in nanometers, while the vertical axis is calibrated in relative intensity units. The graph shows the predominantly UV radiation at left, with the individual emission lines in the visible range shown at right;

FIG. 2 is a schematic diagram of an irradiation system in accordance with the invention.

DETAILED DESCRIPTION

A discharge tube 1 contains a fill gas mixture of noble gases, preferably krypton and argon, with additives of mercury and iron or their halides (e.g. iron iodide) for increased radiation output in the ultraviolet spectral range. The power of the discharge tube is about 2 kilowatts, with an irradiation flux in the UV-A spectral range of more than 500 watts.

Figure 1:
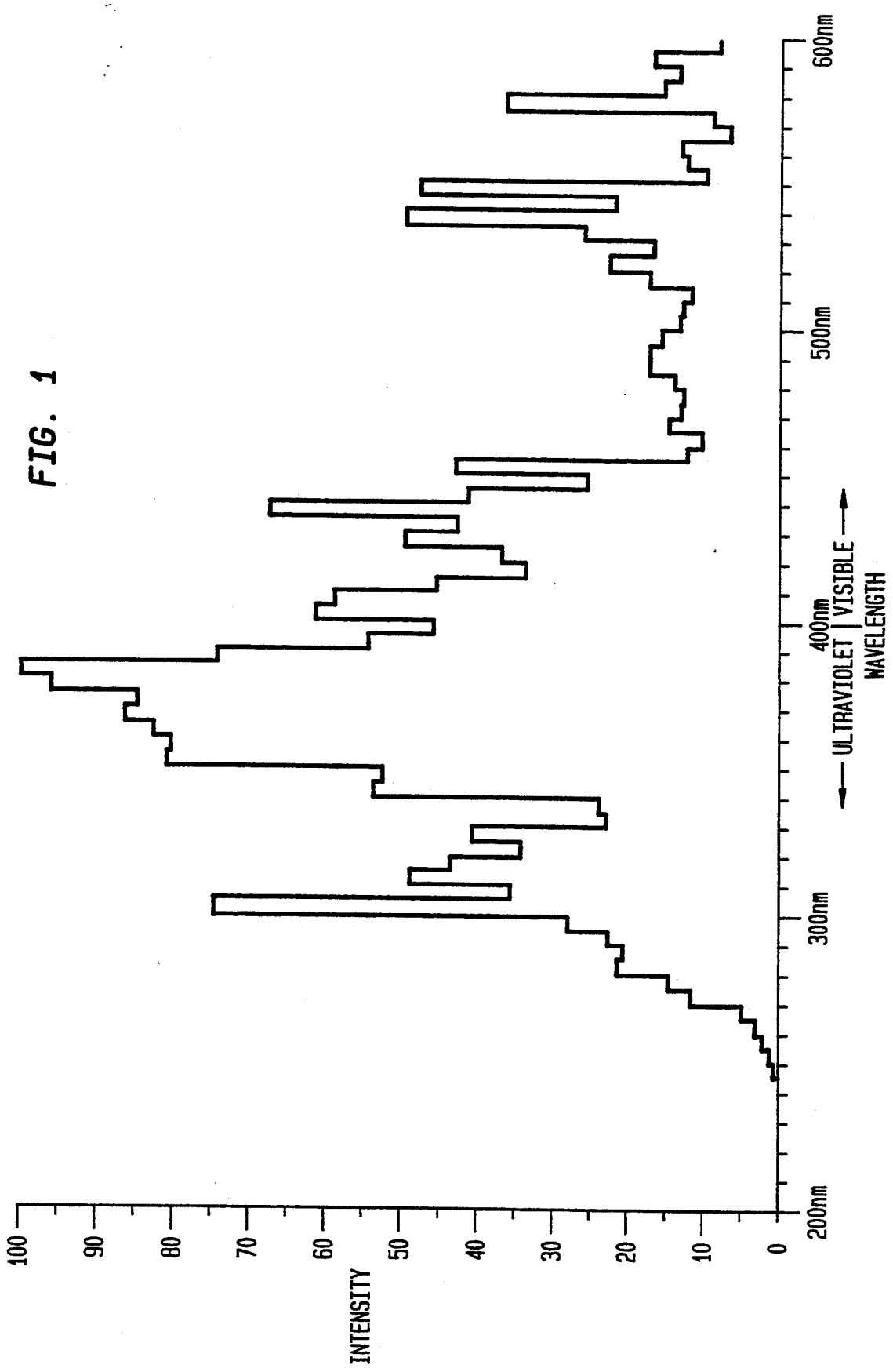
Figure 2:
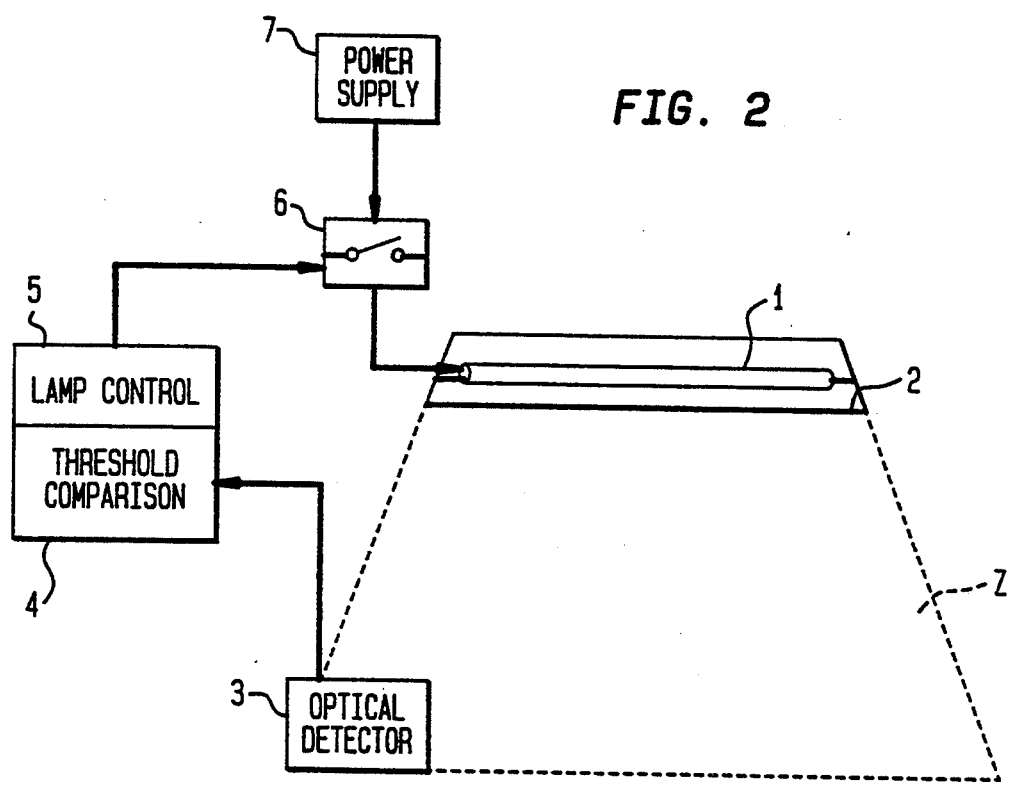

FIG. 1 shows a high intensity in the UV-A range between 320 and 390 nm, and a reduced intensity in the UV-B range between 290 and 320 nm. This remainder intensity is absorbed by a special filter 2. At wavelengths below 250 nm, light emitted by the gas discharge is absorbed by the quartz bulb of the discharge tube. In the visible spectral range, the discharge tube has ranges of lower intensity between blue and green (450–530 nm), between green and yellow (550–580 nm), in red (from 590 nm up) and in the infra-red. The infra-red range is not shown because its intensity is so low by comparison.

The discharge tube of the invention has essentially the same spectrum in the ultraviolet range as the prior art, with the difference that, in one of the aforementioned ranges of lower intensity, one or more emission lines occur because of the marker or further radiation-emitting substance.

As the further radiation-emitting substance, one could select sodium, for example. The yellow sodium lines at 589 and 589.6 nm fall in a favorable spectral region relative to the spectrum emitted by the other fill substances. In practice, the choice of which further radiation-emitting substance to use will depend upon the spectral sensitivity of the optical detector one uses.

Equally well adapted additives are lithium, with its red lines (at 610.4 and 670.8 nm), cesium with its emission lines in the red and infra-red (672.3 and 697.3 and 801.6 and 807.9 nm), and thallium with its green line (535 nm). These could be used instead of sodium.

APPARATUS

In the immediate vicinity of the discharge tube of the invention, within its irradiation zone Z, an optical detector is provided. The detector is preferably a photodiode with special optical filters in front, which let through only a narrow wavelength range, in which the emission line(s) of the further radiation-emitting substance fall. The electrical output signal of the detector is proportional to the integrated intensity in this narrow transmitted spectral range. This output signal is coupled via a threshold comparison stage 4 to a lamp control 5 in such a way that, whenever the output signal drops below a predetermined threshold or minimum amplitude, the lamp is automatically shut off, for example by opening a switch 6 between the lamp and its power supply 7.

The minimum or threshold level of the output signal is determined by measuring the still-present intensity of the detected spectral range after expiration of the service life of the discharge tube. The service life in this example is about 500 operating hours.

By this method, it is made possible that only discharge tubes according to the invention, whose service life has not been exceeded, get installed in ultraviolet irradiation systems. Accidental installation of externally identical discharge tubes, which however have an unsuitable spectral distribution, is rendered impossible. This prevents unsuitable discharge tubes from endangering the success of manufacturing processes or from threatening the health of irradiated persons.

Various changes and modifications are possible within the scope of the inventive concept.

I claim:

1. A self-monitoring irradiation system including
   a discharge lamp (1) filled with a fill mixture of gas and substances having respective characteristic emission lines,
   a plurality of said substances emitting predominantly in a first spectral range; and
   a further radiation-emitting substance contained in said fill, and having an emission line which is in a second spectral range, of lower frequency than said first range,
   an optical detector (3), arranged in an irradiation zone of said discharge lamp, and having a response characteristic such that an output signal of said detector correlates with intensity of said emission line in said second spectral range; and
   lamp control means (5), having an input connected to an output of said optical detector (3), for monitoring of said output signal, and an output interrupting (6) supply of energy to said discharge lamp upon occurrence of:
   insufficient intensity of radiation of said emission line in said second spectral range.

2. A self-monitoring irradiation system according to claim 1, wherein
   said plurality of substances emit predominantly in an ultraviolet spectral range; and
   said emission line of said further radiation-emitting substance is in a visible spectral range.

3. A self-monitoring irradiation system according to claim 2, wherein
   said further radiation-emitting substance is a material selected from the group consisting of
   alkali metals and halides of alkali metals.

4. A self-monitoring irradiation system according to claim 1, wherein
   said plurality of substances emit predominantly in an ultraviolet spectral range; and
   said emission line of said further radiation-emitting substance is in an infra-red spectral range.

5. A self-monitoring irradiation system according to claim 4, wherein
   said further radiation-emitting substance is a material selected from the group consisting of
   alkali metals and halides of alkali metals.

6. A self-monitoring irradiation system according to claim 1, wherein
   said further radiation-emitting substance is a halide of an element selected from the group consisting of sodium, lithium, cesium, and thallium.

7. A self-monitoring irradiation system according to claim 1, further comprising
   threshold comparison means (4) coupled to said lamp control means (5), monitoring amplitude of said output signal and, whenever said amplitude drops below a predetermined threshold value, directing said lamp control means (5) to turn off (6) said discharge lamp (1).

8. A self-monitoring irradiation system according to claim 1, wherein
   said lamp control means also interrupts supply of energy to said discharge lamp upon occurrence of:
   unsuitable spectral distribution of radiation emitted by said lamp (1).

9. A method of operating a gas discharge lamp emitting predominantly in an ultraviolet spectral range and also at an emission line in a non-ultraviolet spectral range,
   comprising the steps of
   comparing emission intensity at said non-ultraviolet emission line with a predetermined threshold intensity value indicative of satisfactory lamp performance, and
   discontinuing lamp operation whenever said emission intensity drops below said predetermined threshold intensity value.

* * * * *